US00PP35085P2

(12) United States Plant Patent
Li

(10) Patent No.: US PP35,085 P2
(45) Date of Patent: Apr. 4, 2023

(54) ***VERBENA* PLANT NAMED 'KLEVP21043'**

(50) Latin Name: ***Verbena* x *hybrida***
Varietal Denomination: KLEVP21043

(71) Applicant: KLEMM + SOHN GMBH & CO. KG, Stuttgart (DE)

(72) Inventor: Ruijun Li, North Parramatta (AU)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/838,413

(22) Filed: Jun. 13, 2022

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 6/86
See application file for complete search history.

*Primary Examiner* — Anne Marie Grunberg
(74) *Attorney, Agent, or Firm* — Weatherly IP Solutions, LLC; James M. Weatherly

(57) ABSTRACT

A new *Verbena* plant particularly distinguished by a semi-mounding to trailing plant habit, and dark violet and light purple flowers, is disclosed.

1 Drawing Sheet

Genus and species: *Verbena* x *hybrida*.
Variety denomination: 'KLEVP21043'.

BACKGROUND OF THE NEW PLANT

The present invention comprises a new and distinct variety of *Verbena*, botanically known as *Verbena* x *hybrida*, and hereinafter referred to by the variety name 'KLEVP21043'. 'KLEVP21043' originated from a cross-pollination conducted in January 2016 in Cobbitty, New South Wales, Australia between the proprietary female *Verbena* variety '15.5170' (unpatented), and the proprietary male *Verbena* variety '15.5169' (unpatented).

The seeds from the cross were sown and plants were grown for evaluation, where an individual plant designated 'KLEVP21043' was selected from the group of plants in Cobbitty, New South Wales, Australia in October 2016.

In October 2016, 'KLEVP21043' was first vegetatively propagated by vegetative cuttings in Cobbitty, New South Wales, Australia. 'KLEVP21043' was found to reproduce true to type in successive generations of asexual propagation via vegetative stem cuttings.

SUMMARY

The following are the most outstanding and distinguishing characteristics of this new variety when grown under normal horticultural practices in Stuttgart, Germany and Latina, Italy.

1. A semi-mounding to trailing plant habit; and
2. Dark violet and light purple flowers.

DESCRIPTION OF THE PHOTOGRAPH

This new *Verbena* plant is illustrated by the accompanying photograph which shows the plant's overall plant habit including form, buds, foliage, and flowers. The photograph is of a plant approximately 5-months-old grown outdoors in Stuttgart, Germany in September 2020. The colors shown are as true as can be reasonably obtained by conventional photographic procedures.

DESCRIPTION OF THE NEW VARIETY

The following detailed descriptions set forth the distinctive characteristics of 'KLEVP21043'. The data which define these characteristics were collected from asexual reproductions carried out in Latina, Italy. Data was collected on three-month-old plants grown in a greenhouse in 2019. Color references are to The R.H.S. Colour Chart of The Royal Horticultural Society of London (R.H.S.), 5$^{th}$ edition (2007).

Classification:
- *Family*.—Verbenaceae.
- *Botanical*.—*Verbena* x *hybrida*.
- *Common*.—*Verbena*.
- *Designation*.—'KLEVP21043'.

Parentage:
- *Female parent*.—'15.5170' (unpatented).
- *Male parent*.—'15.5169' (unpatented).

Plant:
- *Growth and branching habit*.—Semi-mounding to spreading.
- *Height (from top of soil)*.—22.0 cm.
- *Width (horizontal plant diameter)*.—37.0 cm.
- *Time to produce a finished flowering plant*.—8 weeks.
- *Time to initiate and develop roots*.—2 weeks.
- *Root description*.—RHS 155B (White), fine fibrous roots.

Stems:
- *Number of branches per plant*.—More than 24.
- *Growth habit*.—Semi-mounding to trailing.
- *Length*.—24.0 cm.
- *Diameter*.—0.22 cm.
- *Internode length*.—1.9 cm.
- *Color*.—RHS 139D (Green).
- *Anthocyanin*.—Absent.
- *Texture*.—Pubescent.
- *Appearance in cross-section*.—Round.

Leaves:

*Arrangement*.—Opposite.

*Immature and mature leaf color*.—Upper surface: RHS 141A (Green). Lower surface: RHS 141C (Green).

*Length*.—4.7 cm.

*Width*.—2.1 cm.

*Shape*.—Lanceolate.

*Apex*.—Acute.

*Base*.—Obtuse.

*Margin*.—Crenate.

*Texture* (*both upper and lower surfaces*).—Pubescent.

*Venation type*.—Pinnate.

*Venation color* (*both upper and lower surfaces*).—RHS 141D (Green).

*Petioles*.—Length: 0.16 cm. Diameter: 0.1 cm. Color: RHS 141D (Green). Texture: Leathery.

Flower buds:

*Shape*.—Tall, cylindrical.

*Length*.—1.4 cm.

*Diameter*.—0.3 cm.

*Color* (*at tight bud*).—RHS N80B (Purple-violet).

Inflorescence:

*Blooming habit* (*flowering season*).—Continuously.

*Lastingness of individual blooms on the plant*.—About 1 week.

*Fragrance*.—Absent.

*Inflorescence type*.—Umbel.

*Length of inflorescence*.—3.8 cm.

*Diameter of inflorescence*.—5.6 cm.

*Number of florets per inflorescence*.—18.

*Peduncle*.—Color: RHS 141A (Green). Length: 2.5 cm. Diameter: 0.18 cm.

Florets:

*Length*.—2.2 cm.

*Diameter*.—2.1 cm.

*Texture*.—Smooth.

*Form*.—Single.

*Corolla tube length*.—1.8 cm.

*Corolla tube color*.—RHS 157B (Green-White).

*Petals*.—Length of lobe: 1.9 cm. Diameter of lobe: 0.7 cm. Lobe shape: Obtuse. Apex: Emarginate. Base: Fused. Margin: Entire. Texture (both upper and lower surfaces): Glossy, satiny. Color: Immature: Upper surface: Upper two petals RHS N83B; lower three petals RHS N82A with a center of RHS 76B. Lower surface: Upper two petals RHS 77B1 lower three petals RHS N155B. Mature: Upper surface: Upper two petals RHS N81A; lower three petals RHS N82A with a center of RHS 76C. Lower surface: Upper two petals RHS 77B; lower three petals RHS N155B.

*Pedicels*.—Not visible.

Sepals:

*Shape*.—Lanceolate.

*Apex*.—Acute.

*Base*.—Obtuse.

*Margin*.—Entire.

*Length*.—1.2 cm.

*Diameter*.—0.2 cm.

*Color*.—RHS 142C (Green).

*Texture* (*both upper and lower surfaces*).—Hairy, dull.

Reproductive organs:

*Stamens*.—Present. Quantity: 4. Color: RHS 139D (Green). Filament length: 0.27 cm. Filament diameter: 0.1 cm. Anther: Shape: Elliptic. Color: RHS 141D (Green). Length: 0.15 cm. Diameter: 0.1 cm. Pollen amount: Sparse. Pollen color: RHS 2D.

*Pistils*.—Quantity: 1. Length: 1.7 cm. Diameter: 0.1 cm. Stigma: Color: RHS 141D (Green). Appearance: Ovate. Length: 0.1 cm. Diameter: 0.1 cm. Style: Color: RHS 141D (Green). Length: 1.6 cm. Diameter: 0.1 cm.

Fruit and seed set: None observed to date.

Disease and pest/insect resistance: Good tolerance to powdery mildew (*Podosphaera xanthii*).

COMPARISON WITH PARENTAL LINES AND KNOWN VARIETY

'KLEVP21043' is distinguished from its parents as described in Table 1.

TABLE 1

Comparison with Parental Lines

| Characteristic | 'KLEVP21043' | Female parent '15.5170' | Male parent '15.5169' |
|---|---|---|---|
| Earliness to flower | Earlier than both parents | Later than 'KLEVP21043' | Later than 'KLEVP21043' |
| Flower size | Larger than '15.5170' | Smaller than 'KLEVP21043' | Larger than 'KLEVP21043' |

'KLEVP21043' is most similar to the commercial *Verbena* variety 'KLEVP20052' (U.S. Plant Pat. No. 33,856). Differences between the varieties are described in Table 2.

TABLE 2

Comparison with Similar Variety

| Characteristic | 'KLEVP21043' | 'KLEVP20052' |
|---|---|---|
| Growth habit | Semi-mounding to spreading | Upright and round |
| Color of upper two petals, mature | RHS N81A (Dark violet) | RHS 42C |

I claim:

1. A new and distinct variety of *Verbena* plant designated 'KLEVP21043' as illustrated and described herein.

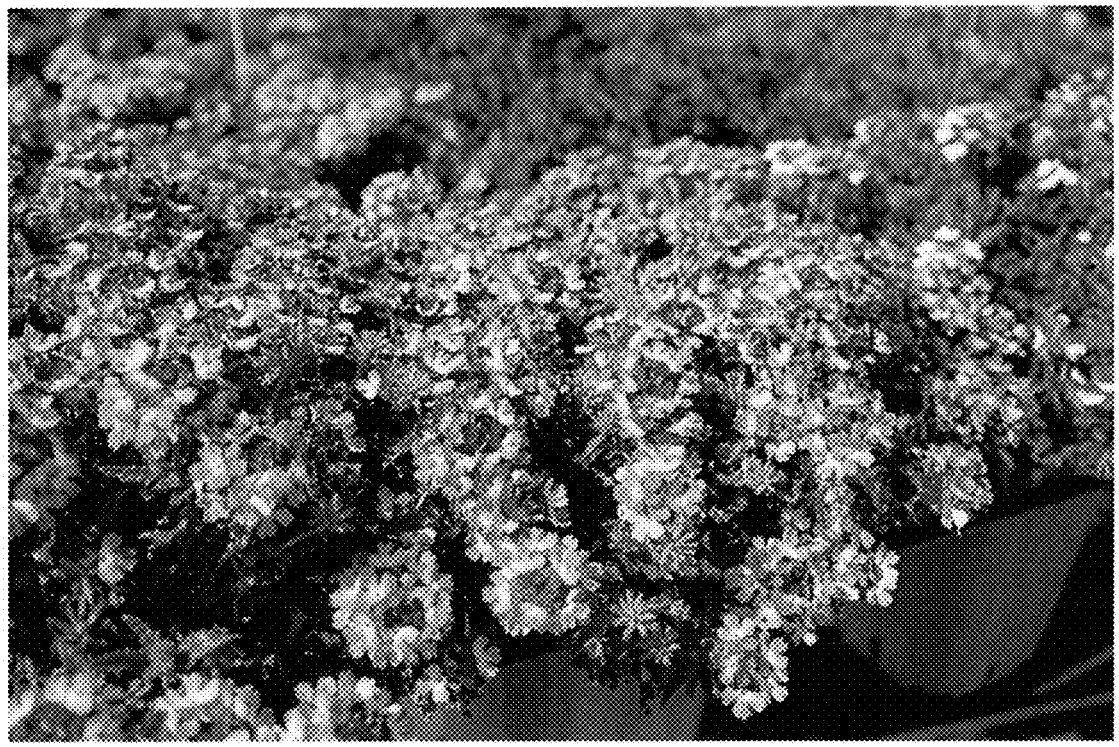

* * * * *